United States Patent
Bushman

Patent Number: 5,613,508
Date of Patent: Mar. 25, 1997

[54] DENTAL FLOSS APPARATUS WITH IMPROVED MECHANISM FOR COLLECTING SPENT FLOSS

[76] Inventor: Rich Bushman, 10975 Stone Bridge Trail North, Stillwater, Minn. 55082

[21] Appl. No.: 385,461

[22] Filed: Feb. 8, 1995

[51] Int. Cl.$^6$ ................................................ A61C 15/00
[52] U.S. Cl. ........................................................... 132/325
[58] Field of Search ................................. 132/322, 323, 132/324, 325, 326, 327, 328

[56] References Cited

U.S. PATENT DOCUMENTS

| | | | |
|---|---|---|---|
| 1,454,429 | 5/1923 | Dresser | 132/325 |
| 3,734,107 | 5/1973 | Thierman | 132/325 |
| 3,746,017 | 7/1973 | Casselman | 132/325 |
| 4,245,658 | 1/1981 | Lecouturier | 132/322 |
| 4,518,000 | 5/1985 | Leverette | 132/325 |
| 4,706,694 | 11/1987 | Lambert . | |
| 4,738,271 | 4/1988 | Bianco . | |
| 4,788,990 | 12/1988 | Wisegerber | 132/324 |
| 4,790,336 | 12/1988 | Kuo | 132/325 |
| 4,807,651 | 2/1989 | Naydich | 132/323 |
| 4,920,992 | 5/1990 | Preciutti | 132/323 |
| 4,920,993 | 5/1990 | Mackie | 132/324 |
| 4,936,326 | 6/1990 | Eckroat | 132/326 |
| 4,941,488 | 7/1990 | Marxer et al. | 132/323 |
| 4,942,894 | 7/1990 | Lai | 132/323 |
| 4,995,361 | 2/1991 | Lorenzana et al. | 132/324 |
| 5,038,806 | 8/1991 | Ewald | 132/325 |
| 5,060,681 | 10/1991 | Westbrook et al. | 132/325 |
| 5,085,236 | 2/1992 | Odneal et al. | 132/324 |
| 5,176,157 | 1/1993 | Mazza | 132/322 |
| 5,183,065 | 2/1993 | Mason | 132/323 |
| 5,186,191 | 2/1993 | Loubier | 132/322 |
| 5,188,133 | 2/1993 | Romanus | 132/325 |
| 5,217,031 | 6/1993 | Santoro | 132/322 |
| 5,267,579 | 12/1993 | Bushberger | 132/322 |
| 5,279,314 | 1/1994 | Poulos et al. | 132/322 |
| 5,287,865 | 2/1994 | Fulton | 132/323 |
| 5,301,698 | 4/1994 | Ballard | 132/325 |
| 5,323,796 | 6/1994 | Urso | 132/322 |
| 5,343,883 | 9/1994 | Murayama | 132/322 |
| 5,348,032 | 9/1994 | Mason | 132/325 |

Primary Examiner—Cary E. O'Connor
Attorney, Agent, or Firm—Patterson & Keough, P.A.

[57] ABSTRACT

The invention is an improved dental floss holder that provides a convenient frame for the flossing of teeth. This dental floss holder allows a user to advance new floss into place ready for use without contact with the floss for improved hygienics and aesthetics. A novel advancing mechanism allows the user to simply advance the floss while holding the handle and moving a knob with a finger. The fresh floss is dispensed from a spool in the handle and the used floss is collected on a separate spool. Both spools are locked during flossing, so the force from flossing does not move the spools. A brake on the dispensing spool ensures that freshly dispensed floss is at the proper tension for use. Alternatively, friction is applied along the path of the floss to supply tension to the floss as it is being dispensed. Broken floss can be easily reattached to the collecting spool. In the preferred embodiment, an empty cartridge containing the dispensing spool can be used to supply an empty collecting spool.

33 Claims, 3 Drawing Sheets

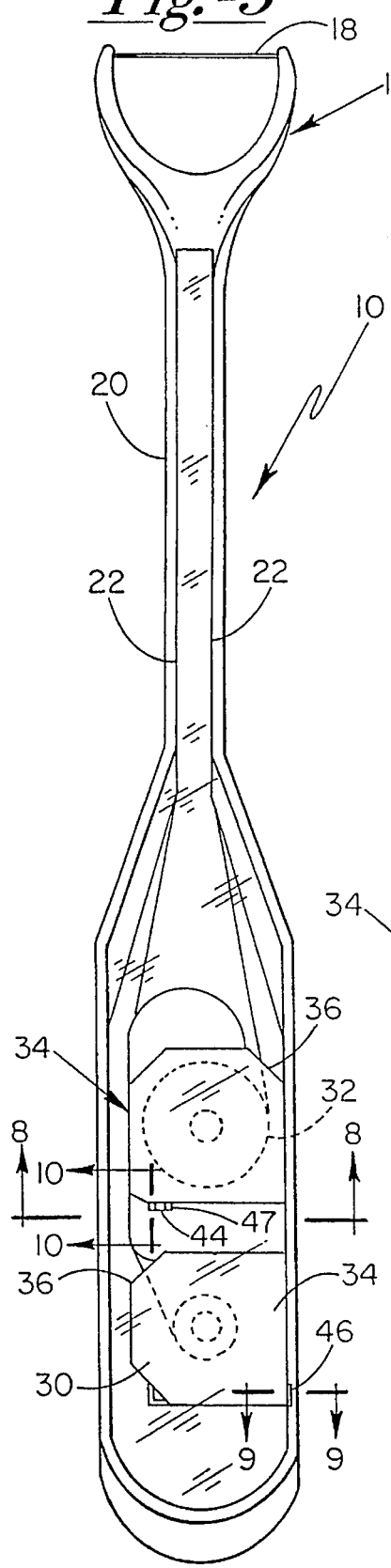
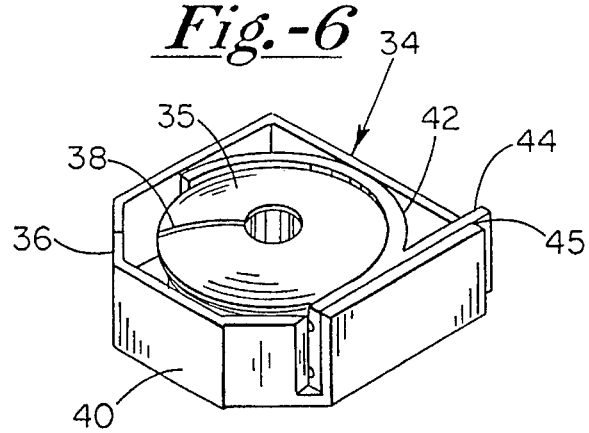
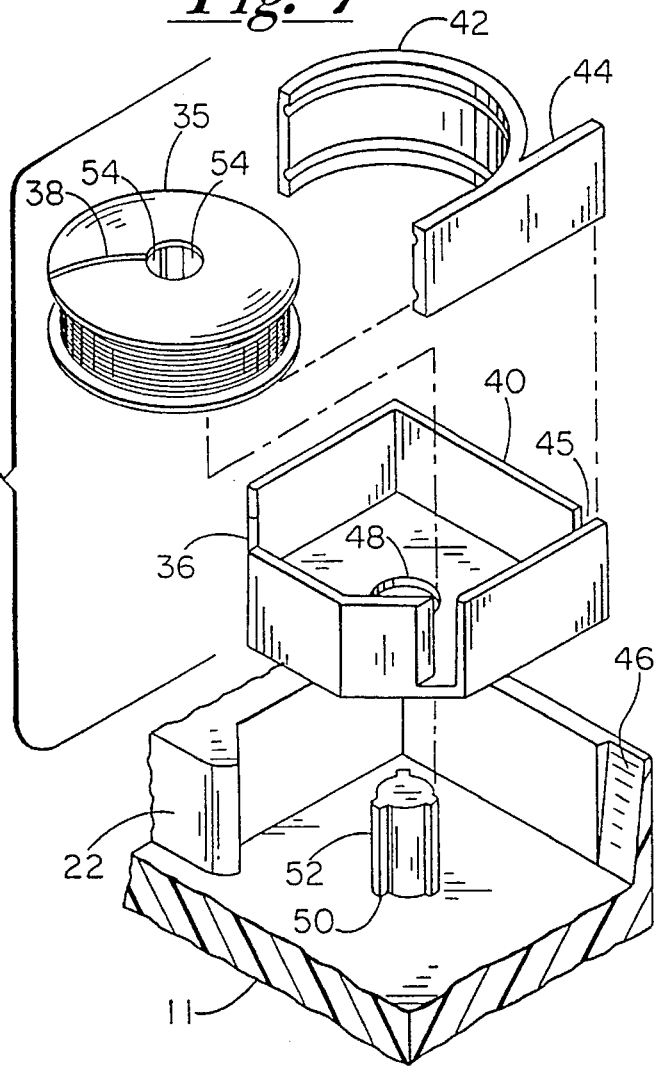

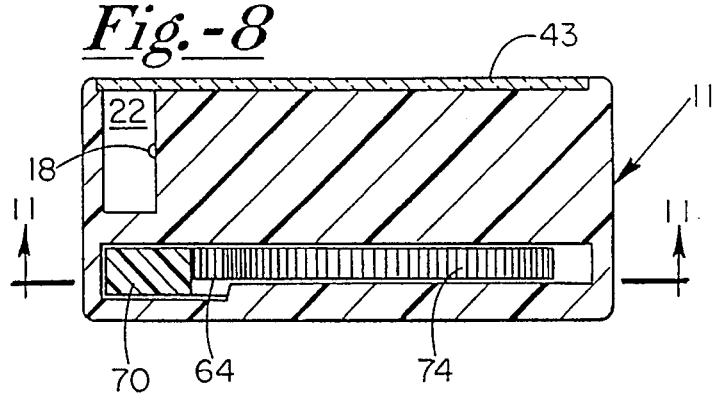
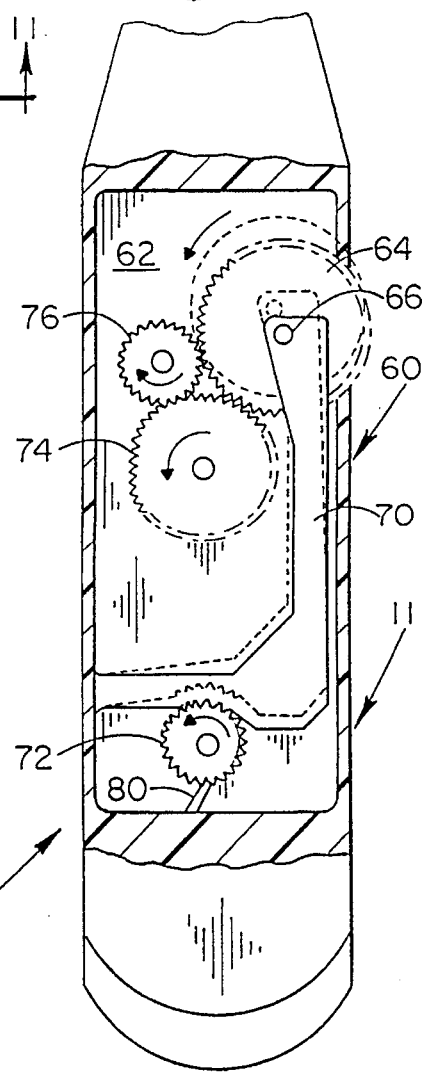
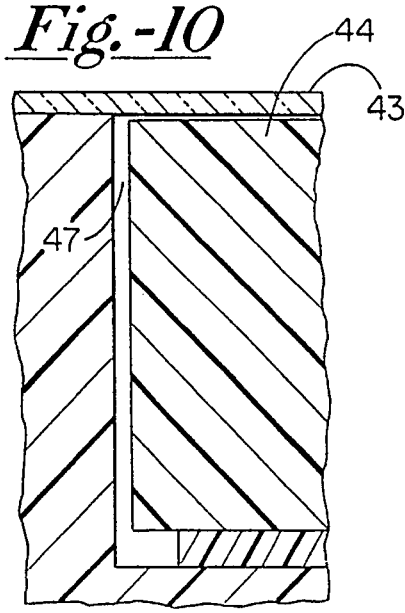
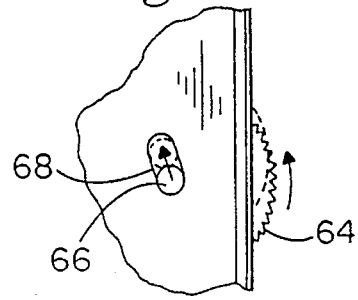

1

DENTAL FLOSS APPARATUS WITH IMPROVED MECHANISM FOR COLLECTING SPENT FLOSS

TECHNICAL FIELD

The invention relates to instruments for aiding the flossing of teeth. More particularly, the invention relates to an improved article for holding floss during the flossing process as well as for dispensing clean floss and collecting used floss with minimal user contact with the floss.

BACKGROUND OF THE INVENTION

Tooth flossing is an important part of the regular maintenance of the health of teeth and gums. In its simplest form, floss is dispensed from a container, and each end of a piece of floss is wrapped around a finger on each of the users two hands. The floss is brought into the mouth for use by the motion of both hands. This can be an awkward procedure under the best of circumstances. It is particularly awkward for a person with limited mobility or in circumstances where a person is flossing the teeth of another person such as a dental technician or a person aiding a disabled person or child. Therefore, various attempts have been made to develop implements for simplifying the flossing procedure.

The flossing apparatuses generally have a divergent or fork-shaped head portion with two prongs for holding a piece of dental floss between them. This head portion replaces the fingers that are used in the manual flossing procedure and is the part of the apparatus which is brought into the mouth for doing the actual flossing. The floss must be held relatively taught between the two ends of the prongs to provide a stiff piece of floss for the user to work between their teeth.

The flossing apparatuses also generally have a handle portion which the user can grasp with one hand. While holding the handle, the user can move the forked floss holding end of the apparatus to a proper location for conducting the flossing. There may also be a neck connecting the fork shaped head portion with the handle portion. The neck may make for greater mobility of the apparatus when the fork shaped head portion is inserted in the oral cavity, especially for reaching rear teeth.

While the designs have differed significantly in the shape and orientation of the handle and a fork shaped head portion, an even greater variation exists in the treatment of the dental floss itself in the apparatus. For example, the dental floss can be fixedly attached to the head portion such that the entire head portion must be replaced to refresh the piece of dental floss in position for use. This arrangement is particularly unsatisfactory since the floss may have to be refreshed quite frequently which would make the necessary replacement of the entire head portion both inconvenient and unnecessarily expensive.

Therefore, several designs of flossing apparatuses have contained dispensing spools within the apparatus to supply a source of fresh floss for replenishing the portion of floss in position for use. These apparatuses have a means for cutting off the spent floss once fresh floss has been delivered across the head of the apparatus for use. A tying portion is provided for holding the floss rigidly against the tension produced when using the floss. These designs are not optimal because the spent portion of the floss must be handled by the user for advancing new floss in position for use and for removing the old floss. This is unpleasant when the user is flossing their own teeth, and unhygienic when the user is flossing the teeth of another person. Furthermore, the procedure is time consuming.

To address the problems associated with the disposal of used floss, several designs have incorporated a spool for the specific purpose of taking up the used dental floss. These designs have various degrees of complexity. Several patents have issued for motorized dental floss apparatuses, for example, U.S. Pat. No. 5,176,157, DEVICE FOR SUPPORTING AND OPERATION OF DENTAL FLOSS, U.S. Pat. No. 5,188,133, DENTAL FLOSSING TOOL, and U.S. Pat. No. 5,323,796, AUTOMATED DENTAL FLOSSER. These motorized dental flossing apparatuses have the disadvantage of being relatively expensive and relatively heavy.

Particularly, the U.S. Pat. No. 5,176,157 patent discloses an apparatus with a dispensing reel and a "truncated cone element" upon which used floss winds around. A motor driven mechanism rotates the truncated cone element and simultaneously rotates a small roller with a swinging motion. The mechanism is designed to run continuously during use to replenish the floss continuously. A dispensing reel is associated with a friction drive means with the amount of friction determined by the screwing or unscrewing of a pawl. It is not clear how the winding up of the floss on the truncated cone element is commensurate with the rotation of the small roller, but it is stated that the floss always remains stretched, even though this would not seem to immediately follow from the design. Periodically, the floss must be cut and removed from the cone element. The main focus of the invention is related to the movement of the floss during use rather than the collection of used floss to minimize handling of the use floss.

A variety of manual dental floss apparatuses with dispensing and collecting spools have been designed. U.S. Pat. No. 4,790,336, DENTAL FLOSS APPLICATOR, describes a device with a supply reel of fresh dental floss and a take-up post. Floss from the supply reel wraps around a reel. Rotation of the reel simultaneously advances floss from the supply reel and rotates the take-up post. Since the amount of floss advanced from the supply reel and the amount of floss collected on the take-up post are not the same amounts, the user must put considerable effort into properly advancing the floss. A floss clip must be used to control the removal of floss from the supply reel. Furthermore, the take-up post is not designed to actually collect a significant quantity of the floss dispensed from the supply reel. Therefore, the clip has a cutting edge for removing much of the floss. Given these limitations in the design of the flossing apparatus of the U.S. Pat. No. 4,790,336 patent, it is not particularly convenient for advancing the floss without handling the used floss, and the user must expend considerable effort to properly advance the floss.

U.S. Pat. No. 5,060,681, DENTAL FLOSSING DEVICE, involves a concentric tapered spool and take-up reel. This device attempts to use the tapered spool to maintain tension in the floss as it is advanced. Since the dispensing spool is tapered, a greater amount of floss is dispensed as more floss is used to account for the greater diameter of the effective collecting spool as floss is collected. For this process to work properly, the floss must unwind and collect perfectly as desired. Also, if any excess floss is introduced, there is no means to take up this excess to allow the device to function with the proper tension again. Perhaps the most serious drawback of this design is that there is no simple way to reattach the floss if it has ripped.

U.S. Pat. No. 5,038,806, DISPOSABLE DENTAL FLOSSER AND HOLDER, describes an apparatus with a spool of unused floss and a take-up reel. The apparatus is designed to approximately dispense and collect like amounts of floss from the respective spool or reel. But the apparatus does not have the means to ensure that the floss remains under tension. Therefore, a guide post is provided for the user to wrap floss around if necessary to increase tension. The spool of unused floss is freely rotatable. This requires an unreasonable amount of interaction by the user to maintain the tension in the apparatus.

Similarly, U.S. Pat. No. 5,301,698, MULTIPLE LOCK DENTAL FLOSS HOLDER AND SPOOL ENCLOSURE ASSEMBLY THEREFOR, discloses concentric dispensing and collecting spools. This apparatus would seem to have no mechanism for adjusting for the different diameters on the dispensing spool and neck upon which the used floss is collected. Therefore, the floss will not remain under tension as the floss is advanced without direct intervention by the user.

Previous designs for dental flossing apparatuses have not provided a mechanism whereby the user can advance the dental floss easily with one hand with a minimum of effort while keeping the floss under sufficient tension to allow flossing. This should be possible with a light, manual apparatus. It should be possible to do inexpensively either with a disposable apparatus or one where the dispensing and collection spools are maintained in cartridges that can be replaced. Such an apparatus would have spools that are locked when the user is not advancing the spool. The apparatus should maintain the tension along the floss while the user is advancing the floss without any effort beyond advancing a knob.

SUMMARY OF THE INVENTION

The advancing mechanism in the flossing apparatus of the present invention locks the dispensing and collecting spools when the user is not advancing the floss. The user moves a knob that causes the collection of used floss onto a collecting spool. The advancing mechanism maintains the tension on the floss while the floss is being advanced, so when the user stops advancing the floss, the floss is at the proper tension for flossing without any further intervention by the user. The flossing apparatus of the present invention preferably has separate cartridges containing the dispensing spool and the collecting spool respectively. The dispensing spool preferably has a curved brake means that engages the dispensing spool to provide generally continuous tension as the floss is dispensed. These cartridges are preferably interchangeable, so the dispensing spool when empty can be put in the place of the collecting spool. The brake in the cartridge would be engaged when the cartridge was used as a dispensing cartridge and not engaged when the cartridge was used as a collection spool.

BRIEF DESCRIPTION OF THE DRAWINGS

FIG. 5 is a top plan view of the dental floss holder;

FIG. 6 is a perspective view of a dental floss cartridge removed from the dental floss holder;

FIG. 7 is an exploded view of a dental floss cartridge above a fragmentary view of the handle of the dental floss holder in the vicinity where a dispensing spool cartridge is placed;

FIG. 8 is a sectional view taken along line 8—8 in FIG. 5;

FIG. 9 is a fragmentary, sectional view taken along line 9—9 in FIG. 5;

FIG. 10 is a fragmentary, sectional view taken along line 10—10 in FIG. 5;

FIG. 11 is a cut away, fragmentary, bottom plan view showing the advancing mechanism within the handle of the dental floss holder; and FIG. 12 is a fragmentary, bottom plan view of a portion of the handle of the dental floss holder near the finger wheel.

DETAILED DESCRIPTION OF THE PREFERRED EMBODIMENTS

Figure 1:
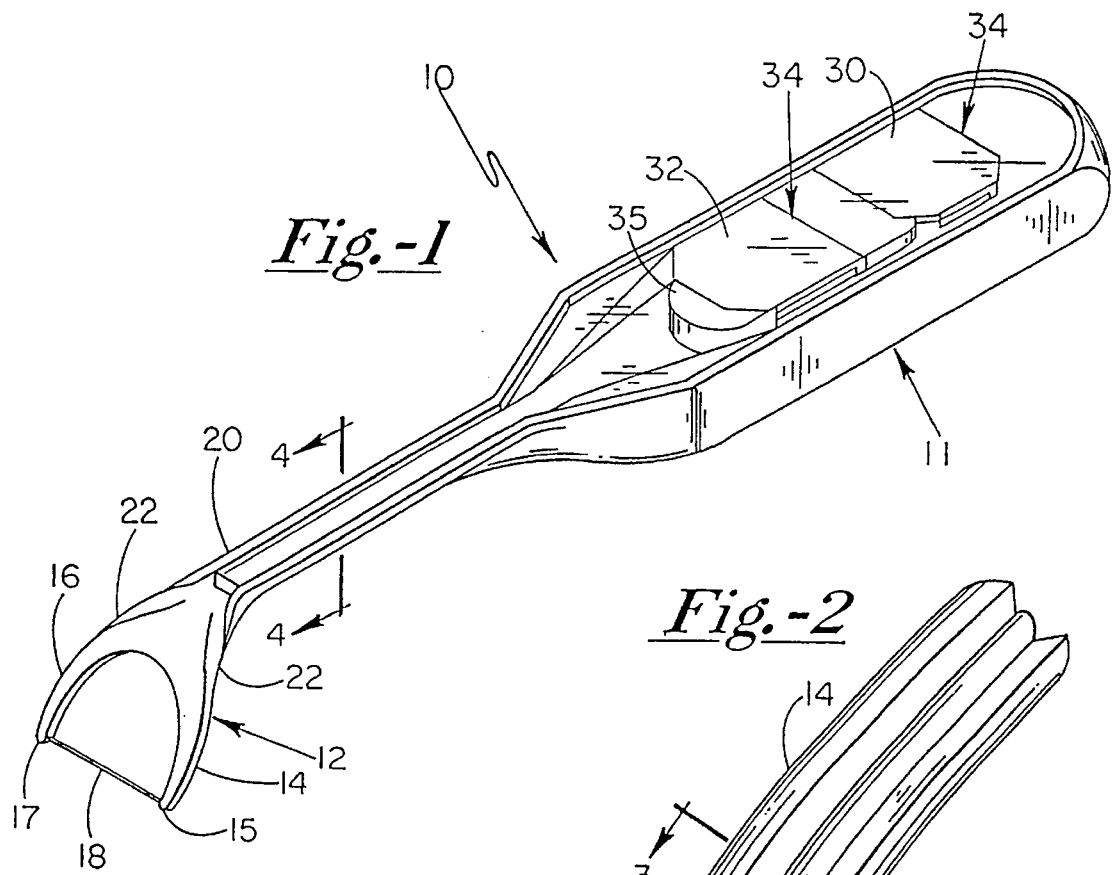
FIG. 1 is a perspective view of a dental floss holder within the present invention.

A dental floss holder 10 of this invention will generally contain a handle 11 and a fork shaped dental floss support 12. The handle 11 is designed to be easily held in one hand by the user. The dental floss support will generally contain two prongs 14, 16 which support dental floss 18 between them during use. The preferred embodiments will have a neck 20 between the handle 11 and the dental floss support 12 to provide improved maneuverability of the floss holder during use. One embodiment (not shown) would allow the reversible folding of the neck relative to the handle to allow for easier transportation with the neck locking in its extended position for use.

Figure 2:
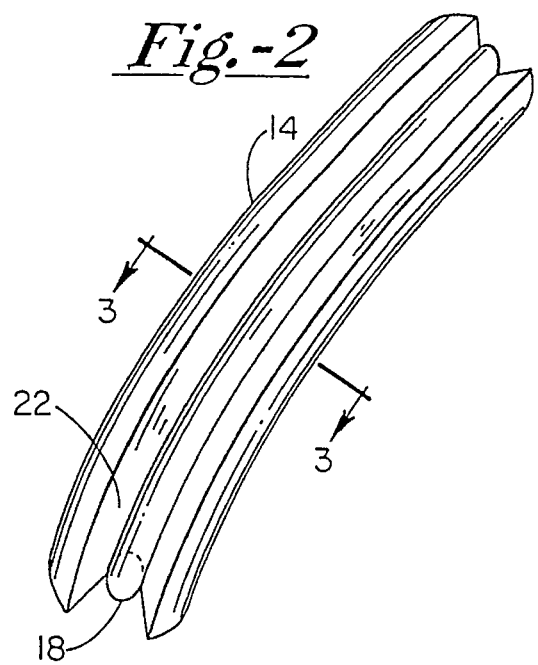
FIG. 2 is an enlarged fragmentary view of one prong of a dental floss support.
Figure 3:
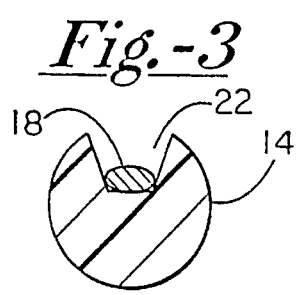
FIG. 3 is a sectional view taken along line 3—3 in FIG. 2.
Figure 4:
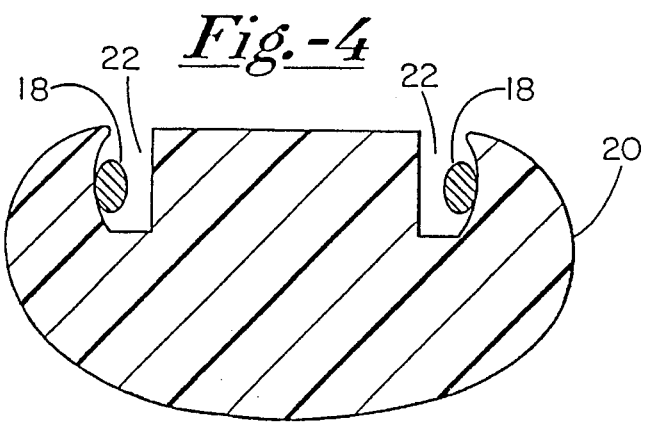
FIG. 4 is a sectional view taken along line 4—4 in FIG. 1.

Each prong 14, 16 of the dental floss support 12 will have a channel 22 for guiding the floss 18. The channel 22 will direct the dental floss 18 to the tip 15, 17 of the respective prong 14, 16. The tips 15, 17 of prongs 14, 16 can optionally have a hole (not shown) or a notch (not shown) to help hold the floss on the tips 15, 17 during use. The channels 22 continue along the neck 20 to direct the floss 18 toward the handle region 11. The channels 22 can be optionally, partially or completely covered to provide for a more aesthetically pleasing dental floss holder 10. FIGS. 2 and 3 display an exposed channel 22 guiding dental floss 18 along one prong 14, 16. FIG. 4 displays a cross sectional view of neck 20 showing two channels 22.

The handle 11 will contain a dispensing reel 30 and a collecting reel 32 which rotate about spaced rotational axes, as shown. Channels 22 extend to handle 11 thereby directing the dental floss 18 to collecting reel 32 and to dispensing reel 30. In a disposable embodiment (not shown), the dispensing reel 30 and the collecting reel 32 are permanently attached to the handle 11. In this embodiment, when the dispensing reel 30 becomes empty, the user throws away the entire device 10. In a preferred embodiment, the dispensing reel 30 and the collecting reel 32 consist of replaceable cartridges. The use of cartridges allows the replacement of the cartridge when the fresh floss 18 is consumed, so the dental floss holder 10 can be continued to be used, resulting in lower overall costs to the user.

In the simplest case (not shown), a spool itself forms the disposable cartridge with one spool forming the dispensing reel 30 and one spool forming the collecting reel 32. Alternatively, a single cartridge (not shown) can be used to constitute both the dispensing reel 30 and the collecting reel 32. Referring to FIGS. 1 and 5, in a most preferred embodiment, an identical separate cartridge 34 is used for both the dispensing reel 30 and the collecting reel 32. The cartridge 34 is designed such that when dispensing reel 30 is empty, the empty cartridge 34 can be moved into position to take the place of the collecting reel 32. The position of the cartridge 34 on the handle 11 determines whether it is serving as a dispensing reel 30 or a collecting reel 32. The replaceable cartridge 34 is properly used as a dispensing reel 30 when it contains fresh floss and a collecting reel 32 after the fresh floss has been consumed.

Referring to FIG. 6, the replaceable cartridge 34 contains a spool 35. Cartridge 34 has an opening 36 to which dental floss 18 passes when the cartridge is serving either dispensing or collecting purposes. The spool 35 within cartridge 34 has an exposed notch 38 which allows for the reattachment of broken floss when the cartridge 34 is being used as a collecting reel 32. FIG. 7 displays the various components of cartridge 34. The spool 35 sits within a base 40. The spool 35 is held in place by a brake element 42. FIG. 8 displays a cross section of handle 11 between dispensing reel 30 and collecting reel 32 with channel 22 containing dental floss 18. An optional, removable cover 43 covers channel 22 and the top of handle 11 in FIG. 8.

Referring to FIGS. 5–7, the brake 42 has movement structure in the form of an extension 44 extending through slot 45 which is engaged by the handle 11 at a notch 46 to guarantee that the brake 42 applies tension against the spool 35 when the cartridge 34 is in the position of a dispensing reel 30. Grooves within brake 42 receive the curved, circumferential edges of the top and bottom portions of the spool 35. When the cartridge 34 is being used to provide a dispensing reel 30, the brake 42 is held against the spool 35 to provide tension during the dispensing of the dental floss 18. Referring to FIG. 9, an engagement element in the form of a sloped notch 46 is shown engaging extension 44 of brake 42 thereby applying pressure from brake 42 to spool 35 to create tension during the dispensing of dental floss 18.

In contrast, as displayed in FIG. 5, the brake 42 will not provide a high degree of tension when the cartridge is in a position to provide a collecting reel 32. Referring to FIG. 10, extension 44 is within a non-engagement element in the form of a cavity 47 with sufficient extra space such that there is no force against extension 44. The brake 42 can optionally have a second extension (not shown) to engage the handle 11 to ensure that significant tension will not be applied to the spool 35 by the brake 42 when the cartridge 34 is in a position acting as a collecting reel 32.

As displayed in FIG. 7, the base 40 of cartridge 34 has a hole 48 opening into the center of spool 35. This allows the insertion of shaft 50 through hole 48 into the center spool 35. Shaft 50 has ridges 52 which engage notches 54 in the center of spool 35. Shaft 50 allows for the control of the rotation of spool 35. One shaft 50 is dispensing support structure used to engage a spool 35 acting as a dispensing reel 30 and the second shaft 50 is collecting support structure used to engage a spool 35 acting as a collecting reel 32.

Referring to FIG. 11, the advancing 1 pivot mechanism 60 is shown within drive cavity 62 in handle 11 below cartridges 34. Finger wheel 64 protrudes from handle 11 allowing a user to rotate the finger wheel 64. The application of torque to finger wheel 64 moves the finger wheel 64 to a second position shown with phantom lines in FIG. 11. A stub 66 protrudes near the center of finger wheel 64. The stub 66 is constrained to move in groove 68 thereby limiting the range of translation of finger wheel 64, see FIG. 12. Phantom lines in FIG. 12 depict the range of motion of stub 66 and finger wheel 64. Finger wheel 64 is also attached to lever arm 70 which elastically moves, i.e. bends and unbends, with the translation of finger wheel 64 as stub 66 slides within groove 68. The relaxed position of lever arm 70 is shown in FIG. 11 by the solid lines. The flex position of lever arm 70 is shown within phantom lines in FIG. 11.

When lever arm 70 is in its relaxed position, lever arm 70 locks dispensing drive wheel 72 preventing its rotation, and finger wheel 64 locks collecting drive gear 74 preventing its rotation. When lever arm 70 is in its fully flexed position as allowed by stub 66, dispensing drive wheel 72 is free to rotate, and the rotation of finger wheel 64 causes the rotation of intermediate gear 76 which in turn causes the rotation of collecting gear 74. Collecting gear 74 is attached to a shaft 50 such that the rotation of collecting gear 74 causes the rotation of shaft 50 which is in position to be inserted into collecting reel 32. Dispensing gear 72 is connected to a shaft 50 in a position where shaft 50 will engage dispensing spool 30. Therefore, when lever arm 70 is in its relaxed position the two shafts 50 respectively engaging the dispensing reel 30 and collecting reel 32 are locked in position thereby preventing their rotation. Catch 80 engaging dispensing gear 72 can ensure the dispensing reel 30 may only rotate in one direction, to dispense dental floss 18. A similar catch (not shown) can be used to limit the rotation of collecting gear 74 in one direction.

Finger wheel 64 can be replaced with various notched levers or other structures to perform comparable tasks. These structures that can function in the role of finger wheel 64 are collectively referred to as knobs. The curved brake 42 can be replaced with other mechanisms for providing friction to the spool 35 in the dispensing reel 30. Furthermore, the tension on the floss can be supplied by applying friction to the floss along its path, for example, by having the motion of the floss maneuver around a projection. An appropriate amount of tension can be designed into the floss path. Similarly, the flexing of lever arm 70 can be accomplished through the use of a separate spring (not shown) rather than relying on the natural elastic properties of the material comprising the lever arm 70. Also, different arrangements of gears can be used to transmit the motion of the user's finger to rotation of the collection spool 32.

Even though there are certain advantages to using a manual version, motorized versions of the present invention are possible. Generally, the braking mechanism can be used effectively in motorized versions of a dental floss holder. With respect to the advancing mechanism 60, a motor (not shown) can be used to rotate spool 35 in collecting reel 32. In this case, lever arm 70 can be flexed to unlock dispensing drive wheel 72 by the motion of the switch (not shown) to actuate the motor. Alternatively, the body of the motor can be attached to lever arm 70 whereby the body of the motor will be designed to move in response to rotation of the motor sufficiently to flex the lever arm 70 unlocking the dispensing drive wheel 72.

The preferred embodiment described above describes a particularly simple and convenient method of construction although others can be used. The distinctive features are the locking of reels 30, 32 when the floss 18 is not being advanced and the rotation of collecting reel 30 caused by the motion of the user's finger. The specific relative orientations of the dispensing reel 30 and the collecting reel 32 are not as important so, for example, they can be concentric. An optional cover can be used to cover some or all of various portions of the dental floss holder 10 including the reels 30, 32, neck 20 and portions of the support 12 along with the channel 22.

When a user is flossing their teeth with floss holder 10, they will release finger wheel 64 such that lever arm 70 will be in its relaxed position locking reels 30, 32. Then, dental floss 18 will rigidly span between prongs 14, 16 of dental floss support 12 allowing the user to work the dental floss 18 between their teeth which applies significant tension on the dental floss 18. When the user desires fresh floss in the useable position along the dental floss support 12, the user will rotate finger wheel 64 flexing lever arm 70 thereby unlocking reels 30, 32.

The subsequent rotation of finger wheel 64 induces the rotation of intermediate gear 76 and collecting gear 74. The rotation of collecting gears 74 causes the rotation of collecting reel 32 thereby causing the collection of additional floss 18 on collecting reel 32. As dental floss 18 is wound around collecting reel 32, tension in the dental floss 18 causes the motion of floss within channel 22 as the floss moves down the handle toward the collecting spool, down the neck towards the handle, across the dental floss support 12, up the opposite side of neck 20 and up the handle from the dispensing reel 30. The dispensing reel 30 will dispense fresh floss in response to the tension once any slack in the floss is wound onto the collecting reel 32. The rotation of finger wheel 64 unlocks the rotation of dispensing reel 30, but the force applied by brake 42 restricts the motion of spool 35.

This restriction on the rotation of dispensing reel 30 by brake 42 causes appropriate tension along the entire length of the dental floss from dispensing reel 30 to collecting reel 32. When the user releases finger wheel 64 and lever arm 70 returns to its relaxed position, the tension created during the dispensing of dental floss 18 will result in relatively taught dental floss spanning between prongs 14, 16 of dental floss support 12. This allows the user to immediately use the dental floss holder 10 without performing any other interactions with the device 10 in order to achieve the proper tension along the dental floss 18. In this way, the user can very easily and quickly place fresh floss in a position to be used without handling the used floss. If the dental floss should break, the user can manually advance sufficient floss, thread the floss along channels 22 and reattach the floss to collecting spool 32 by placing the floss within notch 38. Overall, the user's contact with the dental floss is minimized. While the invention has been described with reference to specific embodiments, the description is intended to be illustrative. Various modifications and changes may occur to those skilled in the art without departing from the spirit and scope of the invention as defined in the following claims.

We claim:

1. An apparatus for holding, dispensing and collecting dental floss comprising:
    a) a handle;
    b) a dental floss support comprising a first projection and a second projection with both projections presenting a tip;
    c) a dispensing reel operably attached to said handle;
    d) a collecting reel operably attached to said handle;
    e) guide means for directing said floss from said dispensing reel, up said first projection, across from said tip of said first projection to said tip of said second projection, down said second projection and to said collecting reel; and
    f) a floss transferring mechanism comprising;
        advancing means for rotating said collecting reel causing the uptake of floss, said rotation of said collecting reel being initiated by the motion of a knob projecting from said handle, with said advancing means preventing rotation of said collecting reel upon release of said knob;
        pivot means for allowing rotation of said dispensing reel upon engagement of said knob while locking said dispensing reel to prevent its rotation when said knob is released.

2. The apparatus of claim 1, wherein said dental floss support is rigidly attached to said handle.

3. The apparatus of claim 1, wherein said dispensing reel and said collecting reel are each comprised of a replaceable cartridge, wherein each cartridge is comprised of a base and a spool with an exposed notch to allow attachment of a loose end of floss to said spool, wherein both replaceable cartridges are operably attachable to said handle and wherein both cartridges comprise structure defining an opening for insertion of a shaft to control rotation of said spool corresponding to said respective reels.

4. The apparatus of claim 3, wherein said dispensing reel replaceable cartridge can be used interchangeably with said collecting reel replaceable cartridge.

5. The apparatus of claim 4, wherein said interchangeable cartridge further comprises brake means for supplying drag to the rotation of said spool when said cartridge is used as a dispensing reel replaceable cartridge and which is essentially released from providing drag when said cartridge is used as a collecting reel replaceable cartridge.

6. The apparatus of claim 3, wherein said dispensing reel replaceable cartridge further comprises brake means for supplying drag to the rotation of said spool to provide generally continuous tension to said floss as said floss is dispensed by said dispensing reel.

7. The apparatus of claim 6, wherein said brake means comprises a curved segment which frictionally engages said spool when said brake means is applied.

8. The apparatus of claim 1, further comprising a neck connecting said handle and said support.

9. The apparatus of claim 1, further comprising brake means for supplying drag to the rotation of said dispensing reel to provide generally continuous tension to said floss as said floss is dispensed by said dispensing reel.

10. The apparatus of claim 1, further comprising friction means for supplying drag to the motion of said floss along said guide means to provide generally continuous tension to said floss as said floss is dispensed by said dispensing reel.

11. The apparatus of claim 1, wherein said dispensing reel and said collecting reel are rigidly attached to a single cartridge.

12. The apparatus of claim 11, wherein said cartridge further comprises brake means for supplying drag to the rotation of said dispensing reel to provide generally continuous tension to said floss as said floss is dispensed by said dispensing reel.

13. The apparatus of claim 1, wherein said advancing means is non-motorized.

14. An apparatus for holding, dispensing and collecting dental floss comprising:
    a) a handle;
    b) a dental floss support comprising a first projection and a second projection with both projections presenting a tip;
    c) a dispensing reel operably attached to said handle;
    d) a collecting reel operably attached to said handle;
    e) an advancement mechanism which can be engaged by the user to cause the collection of floss on said collecting reel and the dispensing of floss from said dispensing reel;

f) tension means for providing generally continuous tension to said floss as said floss is dispensed by said dispensing reel, the tension means comprising a brake element selectively movable into and out of engagement with the dispensing reel, the brake element having an engagement surface that frictionally engages the dispensing reel, the brake element being permanently fixed against rotation with the dispensing reel;

g) a guide for directing said floss from said dispensing reel, up said first projection, across from said tip of said first projection to said tip of said second projection, down said second projection, and to said collecting reel; and h) structure attached to the handle adjacent the dispensing reel to urge the brake element into frictional engagement with the dispensing reel.

15. The apparatus of claim 14, wherein:

the dispensing reel comprises a top portion having a curved circumferential edge and a bottom portion having a curved circumferential edge, the dental floss to be dispensed being wound around the dispensing reel between the top portion and the bottom portion; and the brake element frictionally engages the curved circumferential edges of the top and bottom portions of the dispensing reel.

16. The apparatus of claim 15, wherein the brake element comprises a pair of grooves that receive the curved circumferential edges of the top and bottom portions of the dispensing reel.

17. The apparatus of claim 14, wherein the structure attached to the handle comprises a sloped surface.

18. The apparatus of claim 14, wherein the engagement surface comprises a curved portion pressed against the dispensing reel.

19. A dental floss cartridge comprising:

a spool for dispensing and alternatively for collecting dental floss, the spool including at least one curved, circumferential edge;

a brake element selectively movable into frictional engagement with the curved, circumferential edge of the spool, the brake element including movement structure constructed to move the brake element into frictional engagement with the curved, circumferential edge of the spool only when the spool is disposed to dispense floss, the spool being free to rotate without being substantially braked by the brake element when the spool is disposed to collect floss; and a cartridge housing supporting the spool and the brake element.

20. The cartridge of claim 19, wherein the movement structure constructed to move the brake element into frictional engagement with the curved, circumferential edge of the spool comprises an extension constructed for engagement with structure for urging the brake element toward the spool when the spool is disposed to dispense floss.

21. The cartridge of claim 20, wherein the extension extends through the cartridge housing to engage the structure for urging the brake element toward the spool.

22. The cartridge of claim 20, wherein the movement structure of the brake element comprises an extension of the brake element, the cartridge being in combination with a dental floss dispensing apparatus, the dispensing apparatus comprising:

dispensing support structure for mounting the cartridge in the dispensing apparatus to dispense floss from the cartridge;

collecting support structure for mounting the cartridge in the dispensing apparatus to collect floss into the cartridge, the collecting support structure being spaced from the dispensing support structure;

an engagement element attached to the dispensing apparatus adjacent the dispensing support structure to engage the extension of the brake element of the cartridge and move the brake element into frictional engagement with the spool when the cartridge is mounted on the dispensing support structure; and a non-engagement element attached to the dispensing apparatus adjacent the collecting support structure to accommodate the extension of the brake element to allow the brake element to clear the spool such that the spool can rotate freely without contacting the brake element when the spool is mounted on the collecting support structure.

23. The cartridge of claim 22, wherein the engagement element comprises a sloped surface engaging the extension of the brake element when the cartridge is inserted into the dispensing apparatus to dispense floss.

24. The cartridge of claim 22, wherein the non-engagement element comprises structure defining a cavity in which the extension of the brake element is disposed when the cartridge is inserted into the dispensing apparatus to collect floss.

25. The cartridge of claim 19, wherein the brake element and the cartridge housing are formed of separate pieces.

26. The cartridge of claim 25, wherein the brake element is movably disposed within the cartridge housing.

27. A method of holding, dispensing and collecting dental floss using a dental floss apparatus including a handle, a dental floss support having first and second projections, a dispensing reel operably attached to the handle to dispense new floss, and a collecting reel operably attached to the handle to collect used floss, the collecting reel and dispensing reel rotating about spaced rotational axes, the method comprising:

(a) engaging and rotating a knob projecting from the handle of the dental floss apparatus;

(b) rotating the collecting reel about its rotational axis and collecting dental floss on the collecting reel in response to step (a);

(c) rotating the dispensing reel about its rotational axis, spaced from the rotational axis of the collecting reel, and dispensing dental floss from the dispensing reel in response to step (a);

(d) releasing the knob projecting from the handle of the dental floss apparatus;

(e) preventing rotation of the collecting reel in response to step (d); and (f) preventing rotation of the dispensing reel in response to step (d).

28. The method of claim 27, wherein step (b) includes bending a lever arm to allow rotation of the collecting reel.

29. The method of claim 28, wherein steps (e) and (f) collectively include unbending the lever arm to fixedly engage and lock gearing attached to the collecting reel and the dispensing reel.

30. A dental floss holding, dispensing and collecting apparatus comprising:

a handle;

a dental floss support comprising a first projection and a second projection, both projections presenting a tip;

a dispensing reel operably attached to the handle;

a collecting reel operably attached to the handle;

guide structure for directing the floss from the dispensing reel to the first projection, across from the tip of the first projection to the tip of the second projection, and from the second projection to the collecting reel; and a floss transferring mechanism comprising:

a finger wheel projecting from the handle to initiate rotation of at least the collecting reel upon rotation of the finger wheel, and an advancement mechanism coupled with the handle and the finger wheel to cause the collecting reel to rotate to cause uptake of floss upon rotation of the finger wheel, the advancement mechanism allowing rotation of the dispensing reel upon engagement of the finger wheel and locking the dispensing reel and the collecting reel against rotation when the finger wheel is released.

31. The apparatus of claim 30, wherein the advancement mechanism comprises a lever arm that selectively engages gear teeth associated with the collecting reel and the dispensing reel.

32. The apparatus of claim 31, wherein the a finger wheel is pivotally supported on the lever arm, the apparatus further comprising:

a dispensing gear operably connected to the dispensing reel to rotate with the dispensing reel, the dispensing gear being engaged by the lever arm to prevent rotation of the dispensing gear when the finer wheel is released;

a collecting gear operably connected to the collecting reel to rotate with the collecting reel; and an intermediate gear engaged with the collecting gear and the finger wheel, engagement and rotation of the finger wheel causing the finger wheel to disengage from the collecting gear and causing the collecting gear to rotate via the intermediate gear, and release of the finger wheel causing the lever arm to engage the collecting gear and prevent the collecting gear from rotating.

33. An apparatus for holding, dispensing and collecting dental floss comprising:

a) a handle;

b) a dental floss support comprising a first projection and a second projection with both projections presenting a tip;

c) a dispensing reel operably attached to said handle and comprising a top portion having a curved circumferential edge and a bottom portion having a curved circumferential edge, the dental floss to be dispensed being wound around the dispensing reel between the top portion and the bottom portion;

d) a collecting reel operably attached to said handle;

e) an advancement mechanism which can be engaged by the user to cause the collection of floss on said collecting reel and the dispensing of floss from said dispensing reel;

f) tension means for providing generally continuous tension to said floss as said floss is dispensed by said dispensing reel, the tension means comprising a brake element having an engagement surface that frictionally engages the curved, circumferential edges of the top and bottom portions of the dispensing reel, the brake element being permanently fixed against rotation with the dispensing reel; and g) a guide for directing said floss from said dispensing reel, up said first projection, across from said tip of said first projection to said tip of said second projection, down said second projection, and to said collecting reel.

* * * * *